US00PP13892P39

(12) United States Plant Patent
Pieters

(10) Patent No.: US PP13,892 P3
(45) Date of Patent: Jun. 17, 2003

(54) CHRYSANTHEMUM PLANT NAMED 'GEDI ONE PRA'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 09/873,923

(22) Filed: Jun. 4, 2001

(65) Prior Publication Data

US 2003/0028938 P1 Feb. 6, 2003

(51) Int. Cl.[7] ..... A01H 5/00
(52) U.S. Cl. ..... Plt./293

(58) Field of Search ..... Plt./293, 290, 287, Plt./292

(56) References Cited

U.S. PATENT DOCUMENTS

PP10,213 P 1/1998 Wain ..... Plt./287

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a large, decorative type inflorescence, consistent flowering response to short days, blooming consistently after 49 days of short day length, free branching habit, and highly floriferous plants.

1 Drawing Sheet

LATIN NAME

*Dendranthema morifolium.*

VARIETY

Figure 1:
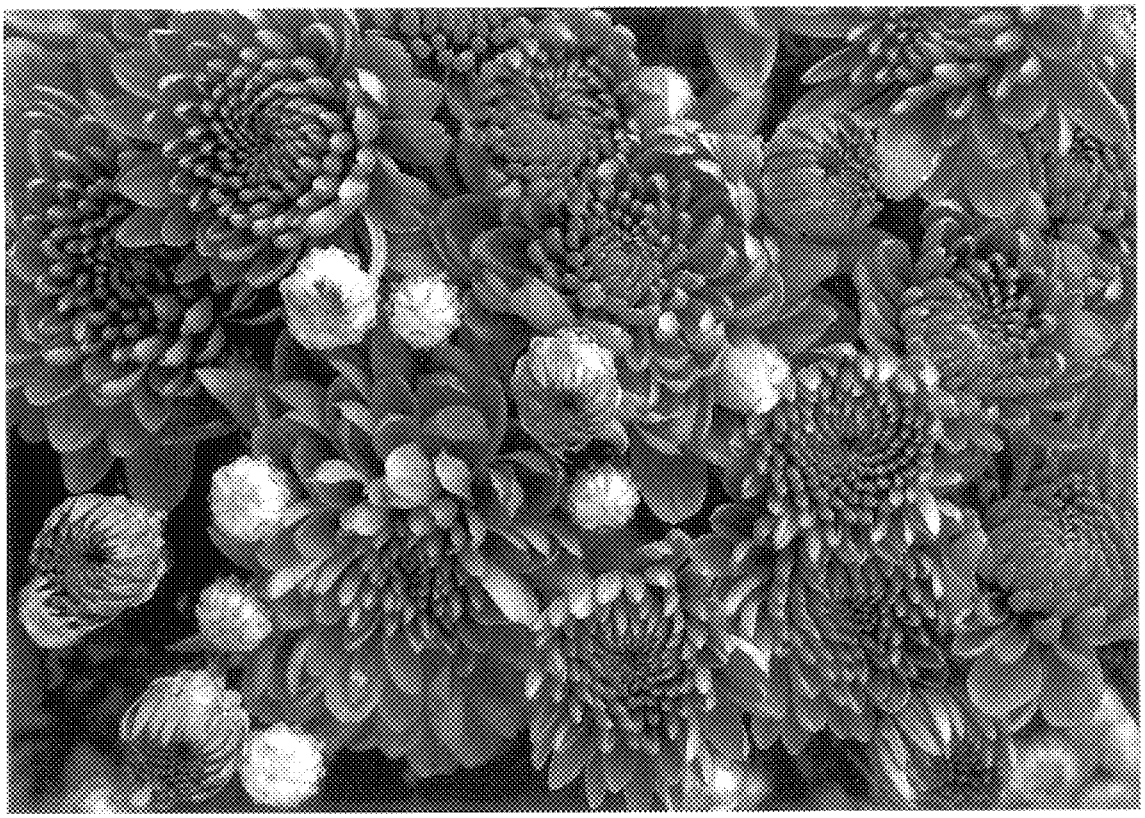

'Gedi One Pra'.

BACKGROUND OF THE INVENTION

The present invention relates to a new and distinct cultivar of Chrysanthemum plant, herein after referred to by the cultivar name 'Gedi One Pra.'

This new cultivar originated from hybridization of a female parent Chrysanthemum cultivar unnamed, undistributed (unpatented in the United States) with a male parent Chrysanthemum cultivar 'Maribelle' (unpatented in the United States). The new cultivar was discovered by the inventor in October 1996.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'Gedi One Pra' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi One Pra.' These characteristics in combination distinguish 'Gedi One Pra' as a new and distinct Chrysanthemum:

1. Large, decorative type inflorescence;
2. Consistent flowering response to short days, blooming consistently after 49 days of short day length;
3. Free branching habit; and
4. Highly floriferous plants.

Plants of the new cultivar are similar to plants of the female parent cultivar in most horticultural characteristics, however plants of the new cultivar differed from plants of the female parent cultivar in the following characteristics:

1. The new cultivar naturally blooms 2 weeks earlier;
2. The new cultivar has larger diameter blooms; and
3. The new cultivar has different color ray florets.

Plants of the new cultivar are similar to plants of the male parent cultivar, 'Maribelle,' in most horticultural characteristics, however plants of the new cultivar differed from plants of the cultivar 'Maribelle' in the following characteristics:

1. The new cultivar has more ray florets;
2. The new cultivar has a more round, uniform plant shape; and
3. The new cultivar has different color ray florets.

The new cultivar can be compared to the Chrysanthemum cultivar 'Jenny Wren' (disclosed in U.S. Plant Pat. No. 10,213). However plants of the new Chrysanthemum differed from the plants of the cultivar 'Jenny Wren' in the following characteristics:

1. The new cultivar has more ray florets;
2. The new cultivar has a more round plant shape and greater branching;
3. The new cultivar has a internode length;
4. The new cultivar has a more flexible plant form; and
5. The new cultivar has more blooms per flowering branch.

BRIEF DESCRIPTION OF THE PHOTOGRAPHS

The photograph shows a close-up view of the blooms, buds, and leaves of 'Gedi One Pra.' The plants were grown under outdoor field conditions.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000, 125 days from rooted cuttings. The growing conditions range from 60° to 65° F. at night to 70° to 85° F. during the day. Measurements and numerical values represent averages of typical flowering types.

Botanical classification: *Dendranthema morifolium* cultivar 'Gedi One Pra'.
Commercial classification: Garden-type Chrysanthemum.
Parentage: Hybridization of female parent Chrysanthemum cultivar (unpatented in the United States) with male parent Chrysanthemum cultivar 'Maribelle' (unpatented in the United States).

PROPAGATION

Time to rooting: 7 to 14 days at approximately 21° C.
Root description: Fine, fibrous.

PLANT

Growth habit: Mounding herbaceous perennial.
Height: Approximately 26 cm.
Growth rate: Moderate.
Plant spread: Approximately 22 cm.
Branching characteristics: Free branching.
Length of lateral branches: Approximately 20 cm.
Number of leaves per lateral branch: Approximately 17.
Stem color: Near 148A.

FOLIAGE

Leaf:
- *Arrangement.*—Alternate single.
- *Average length.*—Approximately 7.4 cm.
- *Average Width.*—Approximately 4.4 cm.
- *Shape of blade.*—Ovate.
- *Apex.*—Acuminate.
- *Base.*—Attenuate.
- *Attachment.*—Stalked.
- *Margin.*—Pinnately lobed and toothed.
- *Texture of top surface.*—Lightly pubescent.
- *Texture of bottom surface.*—Lightly pubescent.
- *Color.— Young foliage upper side:* Near 147B. Young foliage under side: Near 147B. Mature foliage upper side: Near 147A. Mature foliage under side: Near 147B. Venation upper side: Near 137C. Venation under side: Near137C.

Petiole:
- *Average length.*—Approximately 2.6 cm.
- *Color.*—137A.
- *Diameter.*—3 mm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the first 2 weeks in September.
- *Number of inflorescences per stem.*—Approximately 9.
- *Inflorescence diameter.*—Approximately 7.6 cm.
- *Inflorescence depth.*—Approximately 3 cm.
- *Inflorescence longevity on plant.*—Approximately 24–29 days.
- *Persistence.*—Persistent.

Ray florets:
- *Appearance.*—Matte.
- *Texture.*—Smooth.
- *Average number per flower.*—Approximately 320.
- *Shape.*—Oblanceolate.
- *Margin.*—Entire.
- *Apex.*—Obtuse.
- *Length.*—Approximately 4.2 cm.
- *Width.*—Approximately 1.5 cm.
- *Color.— Upper surface at first opening:* Near 42A. Upper surface at maturity: Near 42A. Upper surface at fading: Near 42B. Under surface at first opening: Near 179A. Under surface at maturity: Near 179A. Under surface at fading: Near 179B.

Disc florets:
- *Appearance.*—Shiny.
- *Texture.*—Smooth.
- *Average number per flower.*—Approximately 20.
- *Shape.*—Cylindric.
- *Apex.*—Obtuse.
- *Average length.*—Approximately 1 cm.
- *Average width.*—Approximately 0.2 cm.
- *Color.*—At first opening: Near 54D. At maturity: Near 1A. At fading: Near 16A.

Peduncle:
- *Length.*—At terminal end (shortest): Approximately 7 cm. At lateral end (longest): Approximately 12 cm.
- *Strength.*—Moderate.
- *Color.*—Near147B.
- *Habit.*—Erect.
- *Surface texture.*—Lightly pubescent.

Inflorescence bud:
- *Length.*—Approximately 1.5 cm.
- *Diameter.*—Approximately 1.3 cm.
- *Form.*—Globular.
- *Color.*—Near 179A.

Phyllaries:
- *Appearance.*—Matte.
- *Texture.*—Lightly pubescent.
- *Number.*—Approximately 20 to 30.
- *Shape.*—Ovate.
- *Margin.*—Entire.
- *Apex.*—Acute.
- *Diameter.*—Approximately 0.4 cm.
- *Length.*—Approximately 0.6 cm.
- *Color.— Upper side. Near* 147B. Under side. Near 147B.

REPRODUCTIVE ORGANS

Ray florets:
- *Number of pistils per flower.*—1.
- *Stigma shape.*—2 branched.
- *Stigma color.*—Near 7B.
- *Style color.*—Near 2C.
- *Stigma length.*—Approximately 1 cm.
- *Stamens.*—Absent.

Disc florets:
- *Number of pistils per flower.*—1.
- *Stigma shape.*—Cylindric.
- *Style length.*—Approximately 0.3 cm.

*Number of stamens per flower*.—Approximately 5.
*Anther shape*.—Tubular.
*Anther color*.—Near 6A.
*Pollen color*.—Near 7A.

OTHER CHARACTERISTICS

Seed production: Commercially, this plant is not used or observed in a stage wherein seeds would be produced. Therefore, seed production has not been observed to date.

Disease resistance: Neither resistance nor susceptibility to diseases and pests have been observed to date in this cultivar.

What is claimed is:

1. A new and distinct variety of Chrysanthemum plant named 'Gedi One Pra' as herein illustrated and described.

* * * * *